(12) United States Patent
Markham

(10) Patent No.: US 8,250,844 B2
(45) Date of Patent: *Aug. 28, 2012

(54) HELICALLY-WOUND CABLE AND METHOD

(75) Inventor: Jacob E. Markham, Vadnais Heights, MN (US)

(73) Assignee: W. C. Heraeus GmbH, Hanau (DE)

( * ) Notice: Subject to any disclaimer, the term of this patent is extended or adjusted under 35 U.S.C. 154(b) by 377 days.

This patent is subject to a terminal disclaimer.

(21) Appl. No.: 12/542,414

(22) Filed: Aug. 17, 2009

(65) Prior Publication Data

US 2010/0093448 A1    Apr. 15, 2010

Related U.S. Application Data

(63) Continuation-in-part of application No. 12/248,471, filed on Oct. 9, 2008, now Pat. No. 8,117,817.

(51) Int. Cl.
*D02G 3/36* (2006.01)
(52) U.S. Cl. .......... 57/213; 57/230
(58) Field of Classification Search .......... 57/212, 57/213, 230
See application file for complete search history.

(56) References Cited

U.S. PATENT DOCUMENTS

| | | |
|---|---|---|
| 3,716,982 A | 2/1973 | Morohashi et al. |
| 3,956,877 A | 5/1976 | Gilmore |
| 4,178,810 A | 12/1979 | Takahashi |
| 5,782,903 A | 7/1998 | Wiktor |
| 5,820,464 A | 10/1998 | Parlato |
| 5,932,035 A | 8/1999 | Koger et al. |
| 6,685,696 B2 | 2/2004 | Fleischhacker |
| 6,726,568 B2 | 4/2004 | Tanaka |
| 7,186,223 B2 | 3/2007 | Hiejima et al. |
| 7,828,710 B2 | 11/2010 | Shifflette |
| 2006/0206192 A1* | 9/2006 | Tower et al. .......... 623/1.11 |
| 2007/0225642 A1* | 9/2007 | Houser et al. .......... 604/93.01 |
| 2008/0306327 A1 | 12/2008 | Shifflette |
| 2009/0088278 A1 | 4/2009 | Sasabe et al. |
| 2011/0034863 A1 | 2/2011 | Hoffa |

FOREIGN PATENT DOCUMENTS

| | | |
|---|---|---|
| WO | 9639956 | 12/1996 |
| WO | WO 2008029857 A1 * | 3/2008 |

OTHER PUBLICATIONS

The Office Action for U.S. Appl. No. 12/248,471 mailed Apr. 1, 2011 (11 pages).

* cited by examiner

*Primary Examiner* — Shaun R Hurley
(74) *Attorney, Agent, or Firm* — Dicke, Billig & Czaja, PLLC

(57) ABSTRACT

A cable includes a first layer of wire helically wound to define a lumen having a lumen diameter. A second layer of wire is helically wound over the first layer. A first end segment of the second layer is configured with a plurality of strands that are fused together. A second end segment of the second layer is configured with a plurality of strands that are fused together.

21 Claims, 5 Drawing Sheets

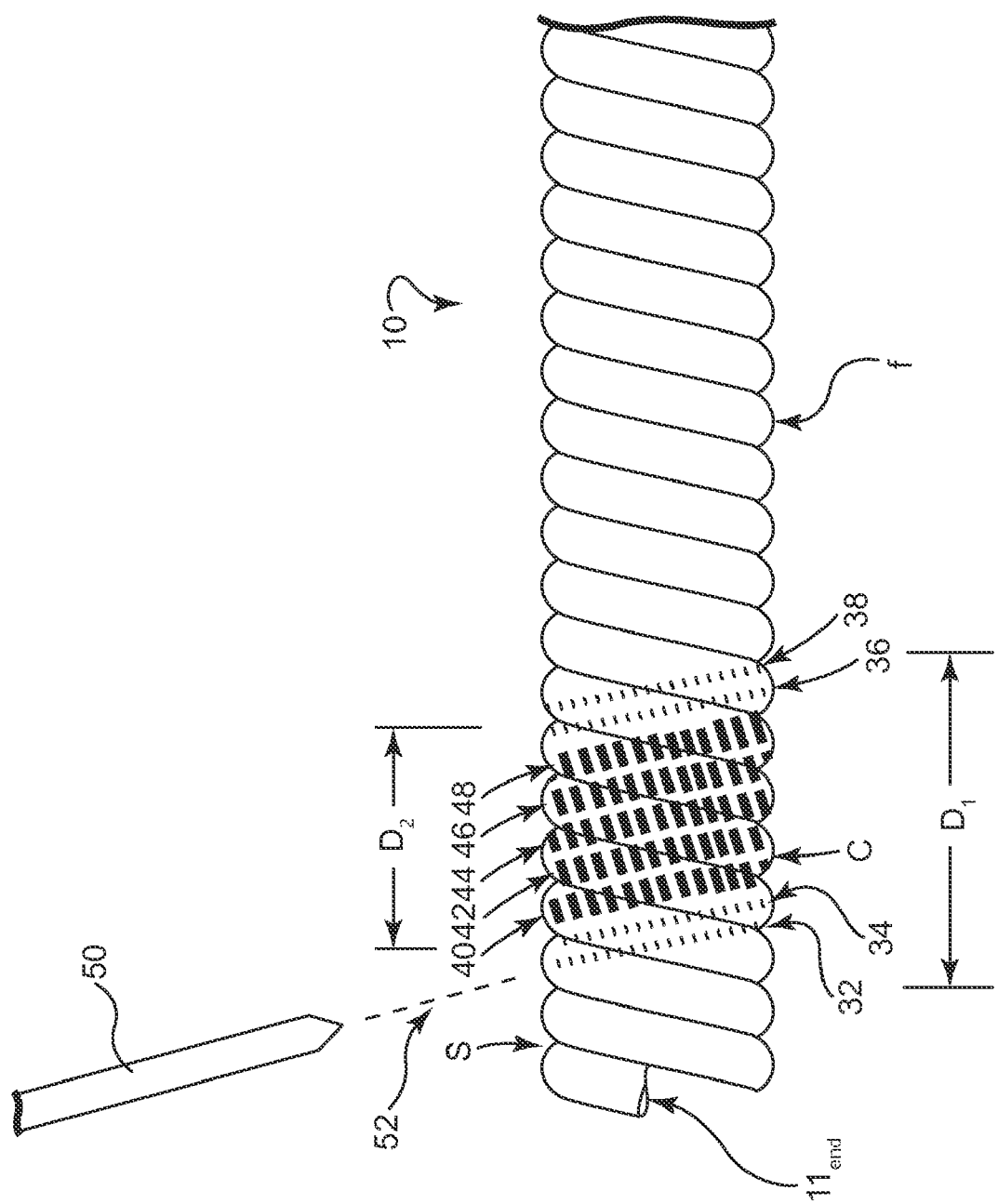

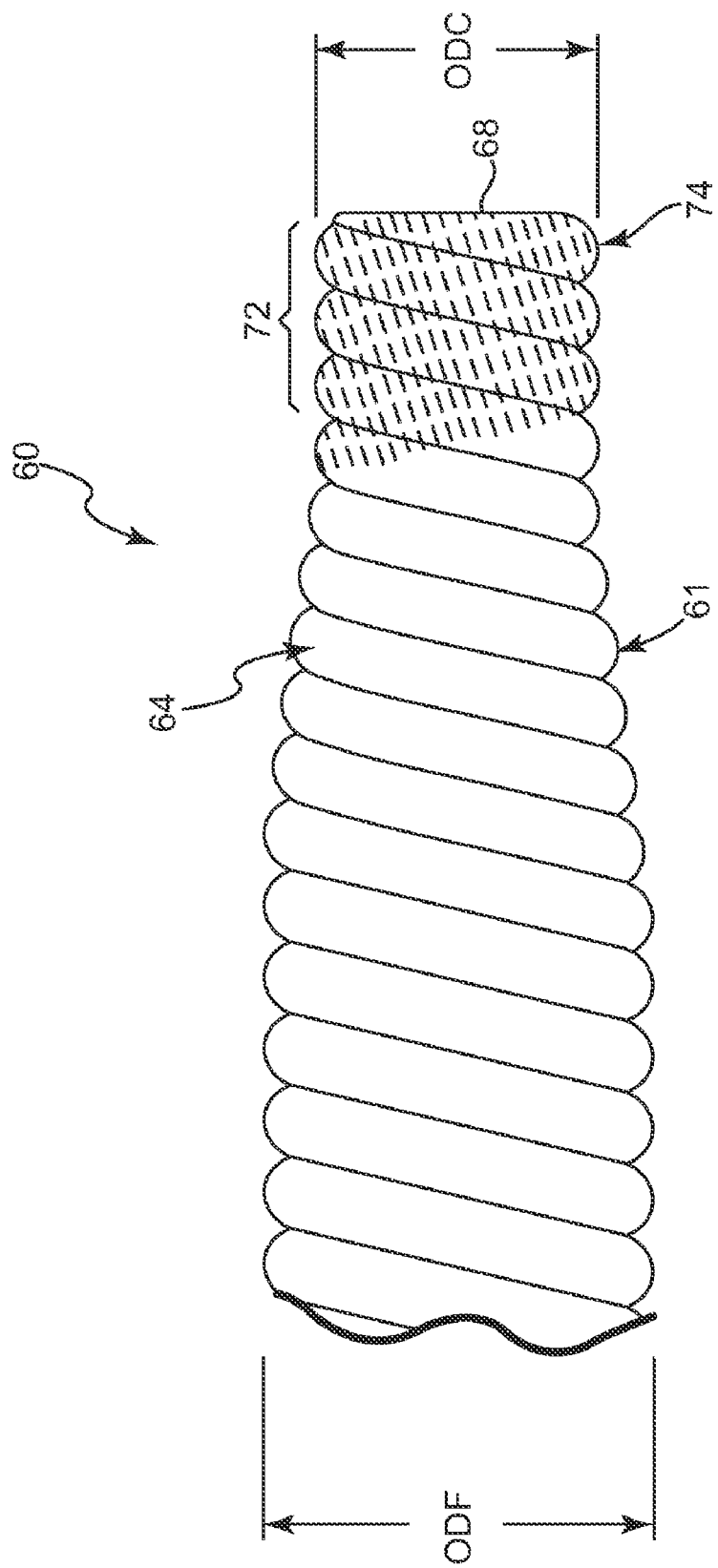

HELICALLY-WOUND CABLE AND METHOD

CROSS-REFERENCE TO RELATED APPLICATIONS

This application is a continuation-in-part of U.S. Ser. No. 12/248,471 filed on Oct. 9, 2008, the disclosure of which is incorporated herein by reference.

BACKGROUND

The present invention relates to helically-wound cable and related method. In one embodiment, the cable includes a single wire that is tightly wound over itself to form a multi-layer cable with a hollow lumen. In some cases, such cables use solder or brazing to secure ends of the cable to prevent its uncoiling. Because there are limitations to use of such approaches, there is a need for the present invention.

BRIEF DESCRIPTION OF THE DRAWINGS

FIG. 4 illustrates a portion of a cable including fuse paths in accordance with one embodiment.

FIG. 5 illustrates a portion of a cable illustrating free and constrained states.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
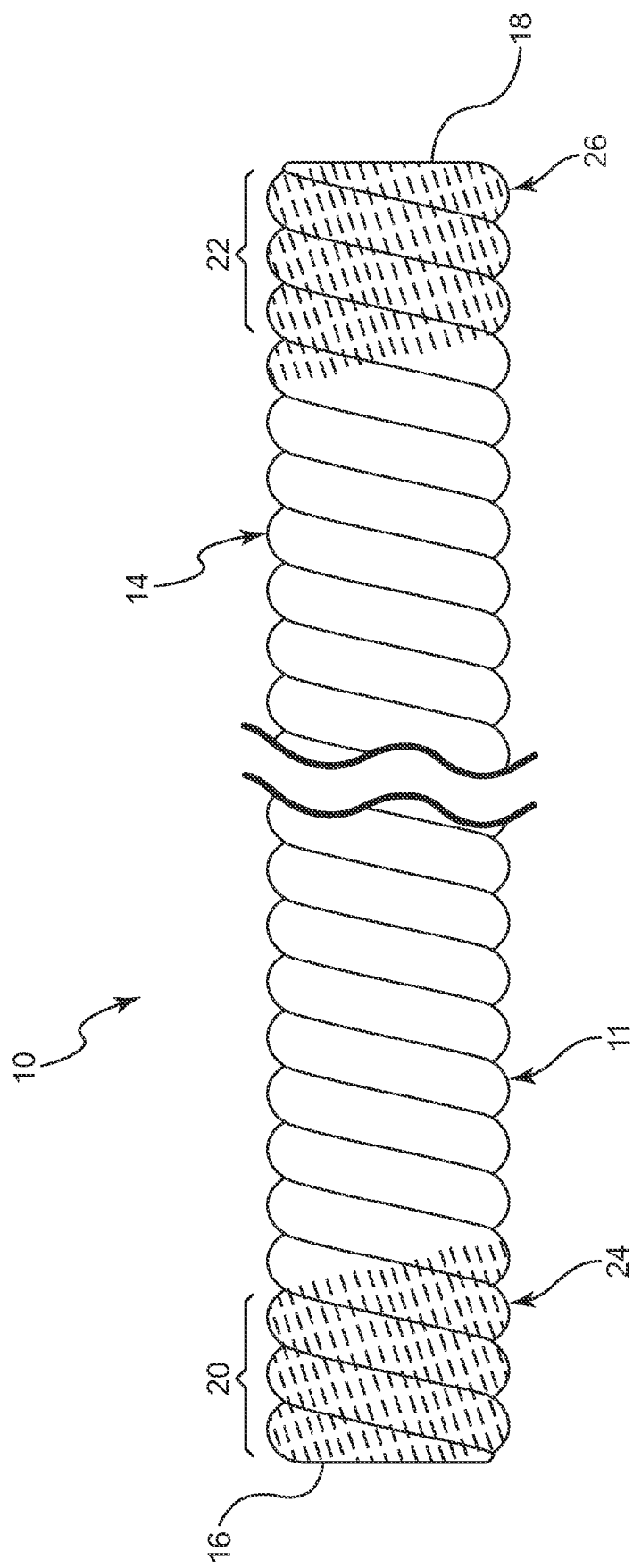
FIG. 1 illustrates a perspective view of a cable in accordance with one embodiment.

FIG. 1 illustrates a perspective view of a helically-wound cable 10 in accordance with one embodiment. In one embodiment, cable 10 is wound with wire 11 and includes a first layer 12 of wire 11 (not visible in FIG. 1) and a second layer 14 of wire 11 that helically wound over the first layer 12. Cable 10 terminates on a first end of cable 10 at a first edge 16 and at a second end at second edge 18. A first end segment 20 is at first edge 16 and a second end segment 22 is at second edge 18. In FIG. 1, cable 10 is illustrated with a truncation in its center, as its length may vary in accordance with particular applications.

In one embodiment, there is first path 24 in first end segment 20 and a second path 26 in second end segment 22. In one embodiment, first and second paths 24 and 26 are fuse paths along which wire 11 in second layer 14 has been melted and then re-solidified. For example, a laser can be directed along first and second paths 24 and 26 and then energized so that wire 11 in second layer 14 is first melted along paths 24 and 26, and then allowed to re-solidify. As illustrated, paths 24 and 26 overlap adjacent strands of wire 11, thereby fusing the two adjacent strands.

In one embodiment, each convolution or helice of wire 11 within first and second end segments 20 and 22 is fused together with each adjacent convolution or helice of wire 11 due to the melting and re-solidifying of wire 11 along paths 24 and 26. In this way, first and second layers 12 and 14 of cable 10 can be held secure without the use of solder or braze anywhere on the cable, even when cable 10 is wound in a constricted state. The fusing of the adjacent convolutions of wire 11 in the first and second end segments 20 and 22 holds cable 10 together and prevents its unwinding.

In the illustration of FIG. 1, paths 24 and 26 are generally helical. In alternative embodiments, paths 24 and 26 can be circular, along the axis of cable 10, random or in various other orientations.

Figure 2:
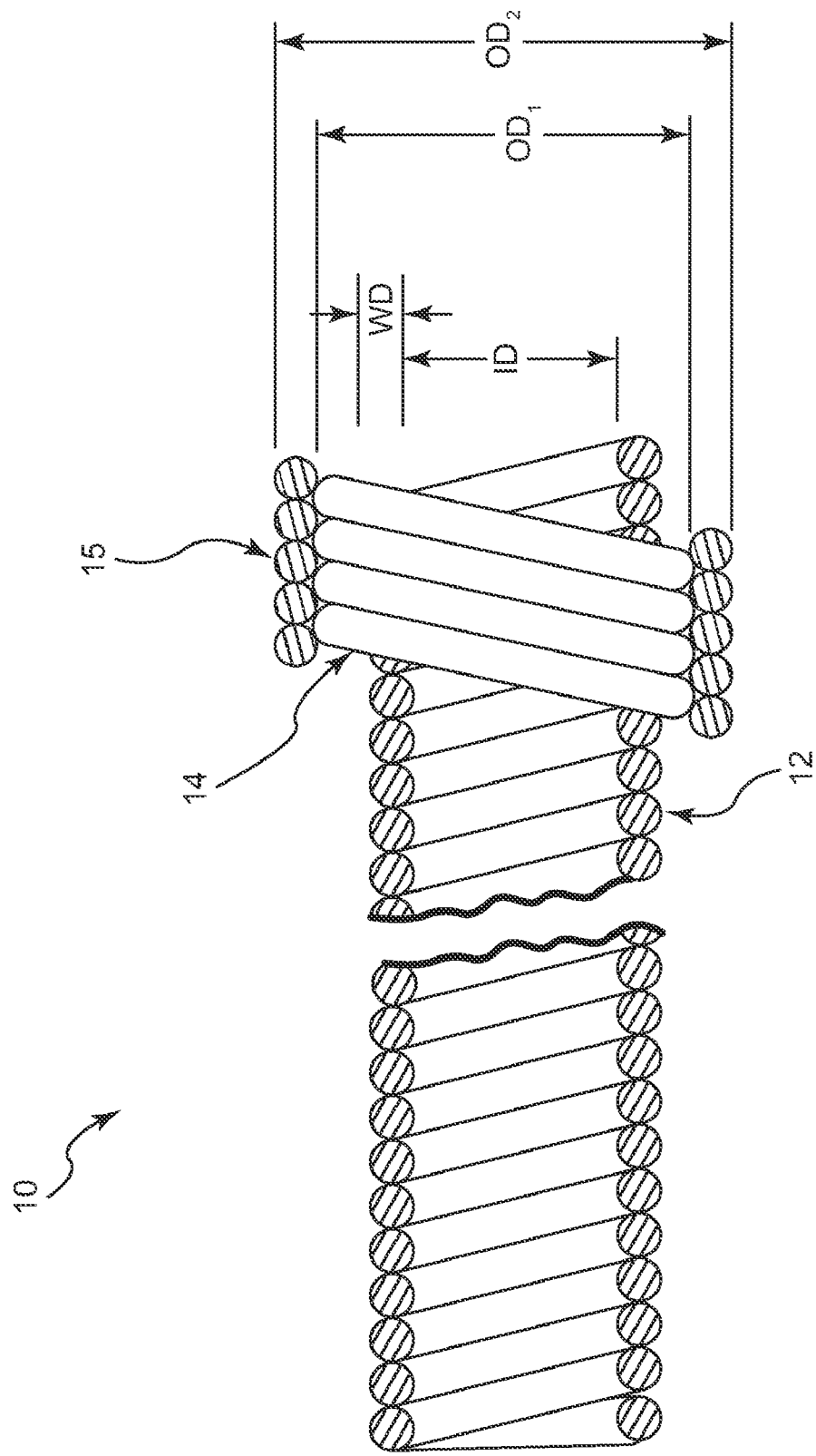
FIG. 2 illustrates in part a side view and in part a cross sectional view of layers of wire of a cable in accordance with one embodiment.

FIG. 2 illustrates partial side view and partial cross-sectional view of cable 10 in accordance with one embodiment. In one embodiment, cable 10 is a "bi-plex" cable having second layer 14 wound over first layer 12. In another embodiment, cable 10 is a tri-plex cable having a third layer 15 wound over first and second layers 12 and 14. First layer 12 is illustrated in cross section and a portion of second layer is illustrated in side view. A portion of third layer 15 is illustrated in cross section.

In the example illustrated in FIG. 2, first layer 12 is helically wound with a pitch in a first direction, while second layer 14 is helically wound with a pitch in a second direction that is reverse relative to the first direction. Reverse winding in this way allows cable 10 to be used in rotating applications without collapsing in or winding open with the rotation of cable 10. In the example where third layer 15 is added over second layer 14, this provides additional stability to cable 10 for bi-directional rotational applications, such that it can be rotated in both clockwise and counterclockwise directions without collapsing in or winding open with the rotation. Such an embodiment may be useful in a rotational application such as in an intravascular ultrasound (IVUS) procedure.

In one embodiment, layer 14 is tightly wound in a constricted state over layer 12 and layer 15 is tightly wound in a constricted state over layer 14 across the entire layer. In one case, a single wire 11 is used for each of first, second and third layers 12, 14 and 15 without ever being cut. In this way, first layer 12 is wound and then second layer 14 is wound back over layer 12 without ever cutting wire 11 that is used to wind the layers. The same can be done for third layer 15 and for any additional layers. As such, there are no pockets between that layers that can cause slippage. In this way cable 10 has excellent "one-to-one" torque, that is, a single full rotation at one end results in a single full rotation at the opposite end, rather than something less than a full rotation.

In one embodiment, cable 10 is configured for very small applications. In some examples, the wire in first, second and third layers 12, 14 and 15 has a wire diameter (WD) as small as 0.0005 inches up to 0.004 inches. In some examples, cable 10 has an inner diameter (ID) as small as 0.008 inches up to 0.03 inches, which also defines the diameter of the lumen within first layer 12 for cable 10. In one bi-plex example (which includes first and second layers 12 and 14), cable 10 has an outer diameter ($OD_1$) of 0.01 inches. In one tri-plex embodiment (which includes first, second and third layers 12, 14 and 15), cable 10 has an outer diameter ($OD_2$) of 0.055 inches. In one embodiment, wire 11 is stainless steel. Different OD and ID sizes for cable 10 are also possible where various different size wire is used.

Figure 3:
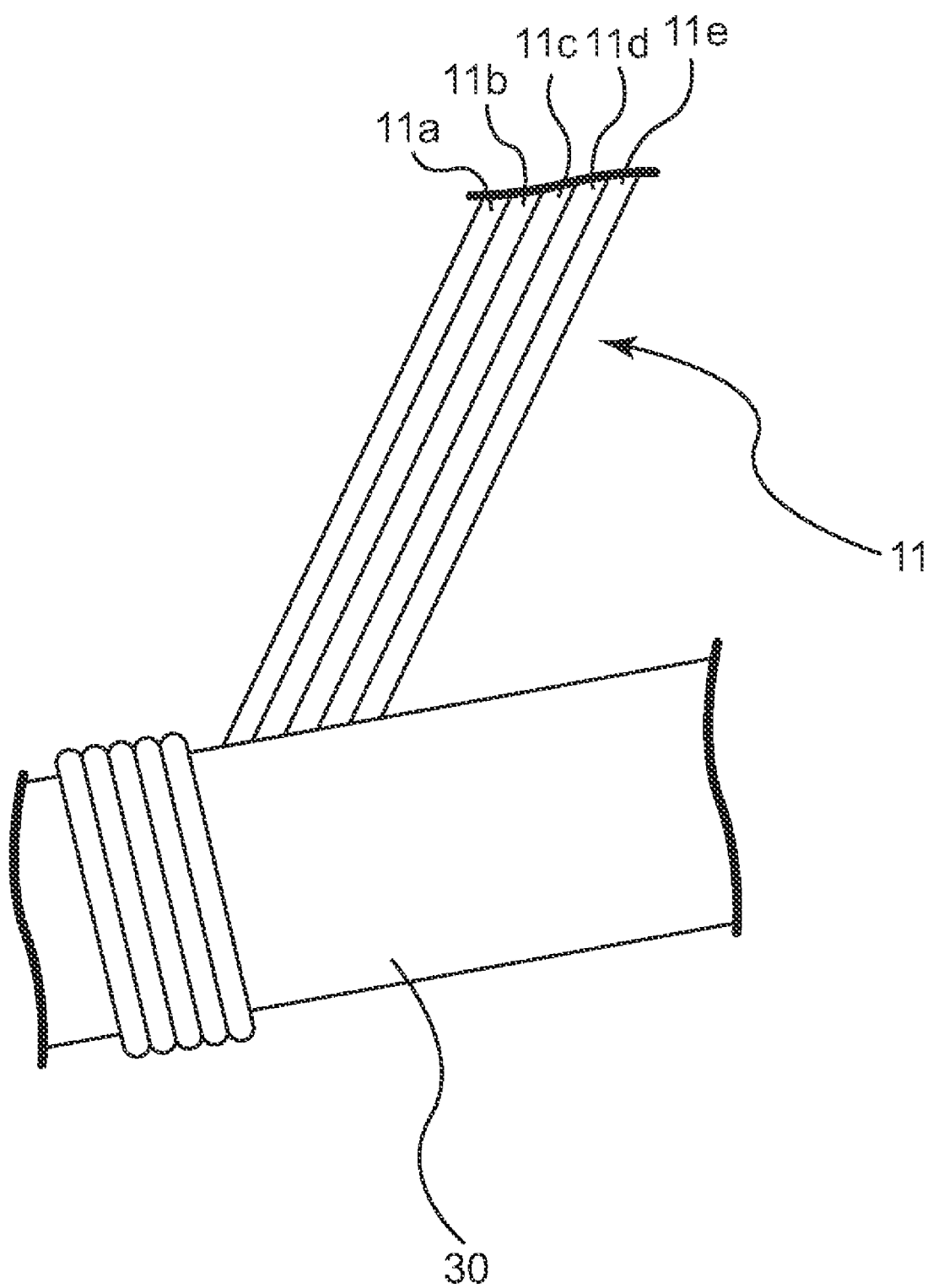
FIG. 3 illustrates a portion of a partially assembled cable in accordance with one embodiment.

First, second and third layers 12, 14 and 15 can be wound in variety of ways. In one embodiment, one convolution of wire 11 is wound at one time for each of layers. In another embodiment, cable 10 is a multifiler cable, where multiple convolutions of adjacent wire 11 are wound at once. FIG. 3 illustrates a mutilfiler cable example, where first layer of wire 12 is being wound over a mandrel 30. In the example, first layer 12 is wound with five adjacent wire helices 11a, 11b, 11c, 11d and 11e at one time. This process continues until first layer 12 is completed. Then, without cutting any of the wire 11, second layer 14 is wound directly over first layer 12, winding wire 11 back onto itself. Third layer 15 or additional layers can be added as well. Each of the layers is in a constricted state.

Once the final layer is wound, wire 11 needs to be secured so that cable 10 will not unravel. In accordance with one embodiment, the final layer, for example second layer 14 in FIG. 1, or third layer 15 in FIG. 3, is secured by fusing adjacent strands of wire 11 to each other in first end segment 20 and/or second end segment 22.

FIG. 4 illustrates a portion of cable 10 that has been fused in accordance with one embodiment. In the illustration, a final layer f is visible. Final layer f is that last layer that is wound over previous layers, and can be second layer 14, third layer 15 or even a fourth or other additional layers of cable 10. Once the winding of cable 10 is complete, wire 11 can be cut establishing a temporary end portion 11 end. This end portion $11_{end}$ can then be temporarily held in place by soldering or brazing of wire 11 at a soldering point indicated with arrow S. Once fusing of wire 11 is completed, cable 10 will be cut at cut point C, thereby removing any temporary solder or braze from cable 10 if desired.

Fusing wire 11 of final layer f can be accomplished in a variety of ways. In one embodiment, cable 10 is located immediately proximate to a laser source 50, which directs a high-intensity light beam 52 at cable 10. Cable 10 can then be moved relative to laser source 50 (or laser source 50 moved relative to cable 10). For example, cable 10 is rotated so that beam 52 impacts cable 10 along a path. In one embodiment, cable 10 is rotated in a helical direction relative to laser 50 such that wire 11 in final layer f is melted along a fuse path where the beam is directed. As indicated previously, other orientations are possible for the fuse path.

In one embodiment as illustrated in FIG. 4, the fuse path along which final layer f is melted is in a helically-shaped path with a pitch in a first direction, while final layer f is helically wound with a pitch in a second direction that is reverse relative to the first direction.

In one embodiment, beam 52 is first directed along a first fuse path while laser 50 is using relatively low power. In this way, wire 11 along the first fuse path is melted only slightly and then re-solidified. First, second, third and fourth sections 32, 34, 36 and 38 illustrate the first fuse path from the use of laser 50 at a lower power setting. Along these illustrated sections 32-38 the area melted by laser 50 and re-solidified is relatively small. There are additional sections of the first fuse path that are not visible in the figure (for example, on the opposite side of cable 10).

Next, beam 52 is then directed along a second fuse path while laser 50 is using relatively high power. In this way, wire 11 along the second fuse path is melted more significantly and then re-solidified. First, second, third, fourth and fifth sections 40, 42, 44, 46 and 48 illustrate the second fuse path from the use of laser 50 at a higher power setting. Along these sections, the area melted by laser 50 and re-solidified is larger relative to those areas in the first fuse path. Each of first-fifth sections 40-48 of the second fuse path cover sections of the first fuse path that were created during a previous pass of the laser. Also, there are additional sections of the second fuse path that are not visible in the figure (for example, on the opposite side of cable 10).

In one embodiment, the first fuse path is defined along a first distance $D_1$ of cable 10. The second fuse path is then defined along a second distance $D_2$. In one example distance $D_2$ is completely contained within first distance $D_1$. In this way, the portion of cable 10 that is subjected to laser 50 at the higher power setting (within second distance $D_2$) has already first been subjected to laser 50 at the lower power setting. As such, wire 11 in that region is less likely to fail or break. If cable 10 is first subjected to laser 50 at the higher power setting, it can damage or even break wire 11, which is wound in a constrained state. If too much power is used for laser 50, especially where wire 11 is relatively thin in diameter, the melting of wire 11 by the high power can allow the tension stored within the constrained wire 11 to break or crack wire 11.

Initially subjecting wire 11 to laser 50 at a lower power setting allows wire 11 to melt and then re-solidify, and thus stabilize, before subjecting wire 11 to laser 50 at a higher power setting. By gradually ramping up the power setting of laser 50 during multiple passes along the fuse paths, more fusing of wire 11 can be achieved without breaking cable 10.

In FIG. 4, a first fuse path with first through fourth sections 32-38 and a second fuse path with first through fifth sections 40-48 are illustrated, but additional fuse paths can also be used to allow the gradual increase in power settings for laser 50. This allows wire 11 of cable 10 to more gradually melt and re-solidify and decreases the risk of cracking and breaking.

Once cable 10 has been sufficiently fused, the temporary soldering or brazing on wire 11 at a soldering point S can be removed if desired. In one embodiment, cable 10 is cut at cut point C, thereby removing any temporary solder or braze from cable 10. This also creates a clean edge for cable 10. FIG. 1 illustrates first and second edges 16 and 18 created in this way by cutting cable 10 after fusing is complete in first and second end segments 20 and 22.

First and second edges 16 and 18 are relatively clean and smooth areas onto which other cables or devices can be attached. Because first and second end segments 20 and 22 are fused together by melting adjacent strands of wire 11 together, no additional materials are added to cable 10. Other than wire 11, cable 10 is thus free of any foreign material, such as braze or solder. Such foreign materials can complicate or weaken the attachment of devices at edges 16 and 18. As such, additional devices can readily be attached to cable 10 at either of edges 16 and 18.

The fusing within first and second end segments 20 and 22 of cable 10 can be done while cable 10 is still supported on a fixture, such as mandrel 30 onto which wire 11 was wound to form cable 10. Mandrel 30 can provide mechanical support within the lumen defined be the inner surface of first layer 12. If cable 10 is first removed from mandrel 30 before fusing, additional support may be needed within the lumen to ensure there is no deformation of the lumen during the fusing process.

Other modifications to the embodiments are also possible. For example, even though FIG. 1 illustrates first and second end segments 20 and 22 with first and second paths 24 and 26, in one embodiment, only a first end segment 20 is used and in that case first path 24 secures cable 10. In this example, cable 10 is wound with a one piece, monolithic or unbroken wire 11 that forms both first layer 12 and second layer 14. As such, even only fusing along first path 24 in first end segment 20 is sufficient to secure cable 10 and prevent its unwinding.

FIG. 5 illustrates a portion of a helically-wound cable 60. In one example, cable 60 is wound with wire 61 and includes a first layer 62 (not visible in FIG. 5) of wire 61 and a second layer 64 of wire 61 that helically wound over the first layer 62. Cable 60 is illustrated as terminating on an end of cable 60 at an edge 68. An end segment 72 is proximate edge 68, and there is a path 74 in end segment 72. Wire 61 in path 74 has been melted and then re-solidified. As such, adjacent strands of wire 61 are fused along path 74 and cable 60 is thereby constricted in end segment 72.

As is the case with cable 10 above, cable 60 is tightly wound in a constricted state. As such, it has stored energy that will release when able. Although cable 60 is fused in end segment 72, in some instances, none of the remaining cable 60 outside end segment 72 is fused. In this way, if there is a failure in cable 60 such as a break, the remaining portions of cable 60 will tend to release and return to a free state from the constricted state in which it is wound. Because cable 60 is wound in a constricted state with stored energy, a break in it will cause a release of this stored energy and an expansion.

Typically, cable 60 will have a larger diameter in its free state than it will in its constricted state. For example, FIG. 5 illustrates where cable 60 has a free state outside end segment 72 and a constricted state within end segment 72. In its free state portion outside end segment 72, cable 60 has an free state outer diameter (ODF), and in its constricted state portion within end segment 72 cable 60 has an constricted state outer diameter (ODC). The free state outer diameter (ODF) is generally larger than the constricted state outer diameter (ODC).

In some applications the free state outer diameter (ODF) cannot be significantly larger than the constricted state outer diameter (ODC). For example, in some embodiments, cable 60 is configured for very small applications, such as where the outer diameter second layer 64 is 0.01 inches. In such small applications, cable 60 may be used within the vascular system of a human. As such, upon failure or break in cable 60, a large increase from the constricted state outer diameter (ODC) to the free state outer diameter (ODF) cannot be tolerated. A large increase in outer diameter could cause damage within the particular application or to the vascular system itself.

In some applications, a restricting cover can be formed or placed over the outer diameter of cable 60 to constrain it even where there is a break or failure of cable 60. In some applications, however, such a cover cannot be used, for example, because of space constraints or other limitations.

In one embodiment, cable 60 is treated to eliminate, or at least to substantially minimize, the difference between the constricted state outer diameter (ODC) and the free state outer diameter (ODF) of cable 60. In one embodiment, cable 60 is subjected to significant heat over a period of time in order to reduce the stored energy within it and reduce the difference between the constricted state outer diameter (ODC) and the free state outer diameter (ODF) of cable 60.

In one embodiment, cable 60 is heated between 20 and 40 minutes at a temperature of between 260 and 700 degrees Celsius. In some applications, heating in this way can reduce the difference between the constricted state outer diameter (ODC) and the free state outer diameter (ODF) of cable 60 from as much as 15 percent or more difference down to less than 1 percent difference.

In this way, where cable 60 is first subjected to this heat treatment before assembled for an application, there will be no significant increase in its outer diameter, even in the case of failure of breakage. Since the difference between the constricted state outer diameter (ODC) and the free state outer diameter (ODF) of cable 60 is reduced to substantially zero, even those portions of cable 60 that are not fused will still not have significant outer diameter expansion.

In some embodiments, however, heating cable 60 at high temperatures can affect the torque response of cable 60. As discussed previously, cables in accordance with various embodiments have excellent one-to-one torque, that is, a single full rotation at one end results in a single full rotation at the opposite end, rather than something less than a full rotation. If cable 60 is subjected to significant heat, this one-to-one torque can be adversely affected. For example, heating cable 60 to 700 degrees Celsius for 30 minutes can cause "wind-up" in the cable. In other words, as one end of cable 60 is rotated, the opposite end does not immediately start to rotate and some of the rotation is absorbed in the coils of cable 60. This is generally not a desired quality for cable 60.

As such, in one embodiment, cable 60 is subjected to the heating process while on a fixture to support the cable and to minimize this wind-up effect. In one embodiment, cable 60 is heated to between 350 and 600 degrees Celsius for 30 minutes. Because of the heat-treatment on the fixture, the difference between the constricted state outer diameter (ODC) and the free state outer diameter (ODF) of cable 60 is reduced to as little as five percent or less. As such, even where there is a failure or break of cable 60, even those portions of cable 60 that are not fused will still not have significant outer diameter expansion. Furthermore, cable 60 will still have excellent torque response, with close to one-to-one torque performance.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A cable comprising:
   A first layer of wire helically wound to define an inner lumen having a lumen diameter;
   a second layer of wire helically wound over the first layer; and
   a first end segment configured with a plurality of strands of wire having at least two adjacent strands fused together;
   wherein each of the first and second layers is heat-treated such that the change in outer diameter of the second layer between its free state and its constrained state is less than 10 percent.

2. The cable of claim 1, wherein each of the first and second layers is heat-treated such that the change in outer diameter of the second layer between its free state and its constrained state is less than 1 percent.

3. The cable of claim 1, wherein heat-treating the first and second layers comprises heating between 20 and 40 minutes at a temperature of between 260 and 700 degrees Celsius.

4. The cable of claim 1, wherein heat-treating the first and second layers comprises heating for approximately 30 minutes at a temperature of between 350 and 600 degrees Celsius.

5. The cable of claim 1, wherein heat-treating the first and second layers comprises heating the layers while they are supported on a fixture.

6. The cable of claim 1 further comprising a third layer of wire over the second layer of wire, wherein the first end segment is in the third layer of wire.

7. The cable of claim 1, wherein the cable is characterized by the absence of solder or braze.

8. The cable of claim 1, wherein the cable is configured for high-speed rotation and one-to-one torque.

9. The cable of claim 1, wherein the lumen diameter is between 0.008 inches and 0.03 inches, the diameter of the cable is between 0.01 inches and 0.055 inches, and the diameter of the wire is between 0.0005 inches and 0.004 inches.

10. A cable comprising:
   a first layer of wire helically wound to define a lumen having a lumen diameter;
   a second layer of wire helically wound over the first layer, the wire in the first and second layers being a single, unbroken piece;
   a first end segment configured with a plurality of strands that are fused together;
   a second end segment configured with a plurality of strands that are fused together; and
   wherein the cable is characterized by the first and second layers having been heated between 20 and 40 minutes at a temperature of between 260 and 700 degrees Celsius.

11. The cable of claim 10, wherein the cable is characterized by the first and second layers having been heated between for approximately 30 minutes at a temperature of between 350 and 600 degrees Celsius.

12. The cable of claim 10, wherein heating the first and second layers causes the change in outer diameter of the second layer between its free state and its constrained state to less than 10 percent.

13. The cable of claim 10, wherein heating the first and second layers causes the change in outer diameter of the second layer between its free state and its constrained state to less than 1 percent.

14. The cable of claim 10, wherein heat-treating the first and second layers comprises heating the layers while they are wound over a fixture.

15. A method of forming a cable comprising:
   winding a first layer of wire over a mandrel thereby defining a lumen having a lumen diameter;
   winding a second layer of wire over the first layer;
   fusing a plurality of strands of wire together in a first end segment of the second layer such that at least two adjacent strands are fused together; and
   heating the first and second layers between 20 and 40 minutes at a temperature of between 260 and 700 degrees Celsius.

16. The method of claim 15 further comprising heating the first and second layers for 30 minutes at a temperature of between 350 and 600 degrees Celsius.

17. The method of claim 15, further comprising heating the first and second layers while they are wound over a fixture.

18. The method of claim 15, further comprising heating the first and second layers such that the change in outer diameter of the second layer between its free state and its constrained state is less than 1 percent.

19. A method of forming a cable comprising:
   winding a first layer of wire over a mandrel thereby defining a lumen having a lumen diameter;
   winding a second layer of wire over the first layer;
   fusing a plurality of strands of wire together in a first end segment of the second layer such that at least two adjacent strands are fused together; and
   heating the first and second layers such that the change in outer diameter of the second layer between its free state and its constrained state is less than 10 percent.

20. The method of claim 19, further comprising heating the first and second layers such that the change in outer diameter of the second layer between its free state and its constrained state is less than 1 percent.

21. The method of claim 19 further comprising heating the first and second layers for 30 minutes at a temperature of between 350 and 600 degrees Celsius.

\* \* \* \* \*